United States Patent [19]

Locatelli et al.

[11] 4,383,118

[45] May 10, 1983

[54] PREPARATION OF GLYCIDYL POLYETHERS OF POLYPHENOLS

[75] Inventors: Jean-Louis Locatelli, Vienne; Gerard Soula, Meyzieu, both of France

[73] Assignee: Rhone-Poulenc Industries, Paris, France

[21] Appl. No.: 296,213

[22] Filed: Aug. 25, 1981

[30] Foreign Application Priority Data

Aug. 27, 1980 [FR] France ............................. 80 18563

[51] Int. Cl.³ .................. C07D 301/28; C07D 301/00
[52] U.S. Cl. ................................... 549/517; 525/121; 528/111
[58] Field of Search ................... 260/348.15; 549/517

[56] References Cited

U.S. PATENT DOCUMENTS

| | | | |
|---|---|---|---|
| 4,269,952 | 5/1981 | Locatelli | 260/348.15 |
| 4,273,915 | 6/1981 | Soula et al. | 260/348.15 |
| 4,276,406 | 6/1981 | Monnerat et al. | 260/348.15 |
| 4,284,573 | 8/1981 | Arnett et al. | 260/348.15 |
| 4,314,086 | 2/1982 | Soula et al. | 260/348.15 |

OTHER PUBLICATIONS

Georg Manecke et al., Pure & Appl. Chem., vol. 51 (1979) pp. 2313-2330.

*Primary Examiner*—Norma S. Milestone
*Attorney, Agent, or Firm*—Burns, Doane, Swecker & Mathis

[57] ABSTRACT

Glycidyl polyethers of polyphenols are prepared by reacting at least one alkali metal salt of a polyphenol with at least one 1-halogeno-2,3-epoxyalkane, in an anhydrous and essentially aprotic reaction medium, and in the presence of a catalytically effective amount of a catalyst which comprises a cross-linked organic polymeric support, said support having a plurality of catalytically active functional groups covalently coupled thereto, the free valence of said functional groups having the structural formula:

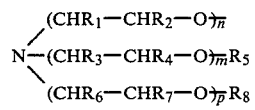

The subject process is admirably suited, for example, for the preparation of epoxy resins from the disodium salt of bisphenol A and epichlorohydrin.

24 Claims, No Drawings

PREPARATION OF GLYCIDYL POLYETHERS OF POLYPHENOLS

BACKGROUND OF THE INVENTION

1. Field of the Invention

The present invention relates to the preparation of glycidyl polyethers of polyphenols, and, more especially, to the preparation of such glycidyl polyethers from alkali metal salts of polyphenols and 1-halogeno-2,3-epoxyalkanes.

2. Description of the Prior Art

The subject ethers are commonly designated in this art as simply "epoxy resins". These resins constitute a class of products which are characterized by the presence of oxirane rings

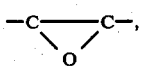

and which, after cross-linking, provide systems or networks having very desirable properties in a number of respects. This has made a broad contribution to the development of this type of resin in numerous fields of application.

Among such resins, those which are conventionally produced by reacting bisphenol A [2,2-bis(4-hydroxyphenyl)-propane] with epichlorohydrin are of very particular value.

SUMMARY OF THE INVENTION

Accordingly, a major object of the present invention is the provision of an improved process for the preparation of glycidyl ethers, in particular the glycidyl ethers of bisphenol A, by reacting alkali metal salts of polyphenols with 1-halogeno-2,3-epoxyalkanes in an anhydrous and aprotic medium.

Another object of the invention is the provision of an improved process which enables the preparation of resins having a viscosity, measured at 25° C., which is less than or equal to 150 poises.

This type of resin is conventionally prepared by reacting bisphenol A with epichlorohydrin in the presence of water and an alkaline agent. A great number of processes for the preparation thereof have to date been proposed to this art. However, these processes are extremely expensive to carry out; they require relatively long reaction times, strict controls over the various reaction conditions and numerous steps for purifying and/or recovering the desired resin. Furthermore, the losses of epichlorohydrin, which is obligatorily employed in excess, are considerable, even when the prior art processes are carried out with the greatest of care.

Very recently, certain authors have envisaged a different method for obtaining this type of resin. Thus, it has been proposed to carry out the synthesis of the resins in question from alkali metal salts of certain diphenols and 1-halogeno-2,3-epoxyalkanes in an anhydrous and aprotic medium (compare *Makromol. Chem.*, 179, 7, 1,661-1,671, 1978).

However, this proposed reaction is strictly limited by the difficulty involved in solubilizing the alkali metal salts of diphenols. In fact, large amounts of dimethyl sulfoxide must be used in order to homogenize the reaction medium, and this severely hinders the development of a technique of this type on an industrial scale.

Briefly, the present invention features the preparation of glycidyl ethers of polyphenols from alkali metal salts of polyphenols and 1-halogeno-2,3-epoxyalkanes, in an essentially anhydrous and aprotic medium, without the necessity that the reaction medium be homogeneous, provided that the reaction is carried out in the presence of certain catalysts.

The process according to the invention enables the obtainment of epoxide resins possessing very good properties, by means of a relatively simple and rapid technique.

DETAILED DESCRIPTION OF THE INVENTION

More particularly according to this invention, at least one alkali metal salt of a polyphenol is reacted with at least one 1-halogeno-2,3-epoxyalkane in the presence of a supported catalyst comprising a cross-linked organic polymeric support and having a plurality of functional groups (active groups of the catalyst) fixed to the said support and having the structural formula:

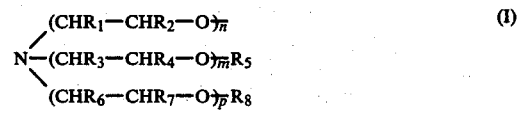

in which $R_1$, $R_2$, $R_3$, $R_4$, $R_6$ and $R_7$, which are identical or different, are each a hydrogen atom or an alkyl radical having from 1 to 4 carbon atoms, $R_5$ and $R_8$, which are identical or different, represent a hydrogen atom, an alkyl or cycloalkyl radical having from 1 to 12 carbon atoms, a phenyl radical ($C_6H_5-$) or a radical $C_6H_5-C_qH_{2q}-$ or $C_qH_{2q+1}-C_6H_4-$, in which q ranges from 1 to about 12 ($1 \leq q \leq 12$), and n, m and p, which are identical or different, are greater than or equal to 1 and less than or equal to 10.

According to a preferred embodiment of the present invention, the functional groups of the catalyst are selected from among the groups of the formula (I) above, in which $R_1$, $R_2$, $R_3$, $R_4$, $R_6$ and $R_7$, which are identical or different, represent a hydrogen atom or a methyl radical and $R_5$ and $R_8$, which are identical or different, represent a hydrogen atom or an alkyl radical having from 1 to 4 carbon atoms.

According to another preferred embodiment of the invention, n, m and p, which are identical or different, are greater than or equal to 1 and less than or equal to 6.

The moieties of the following formulae are exemplary of functional groups suitable for carrying out the subject process:

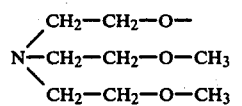

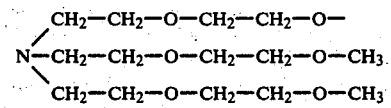

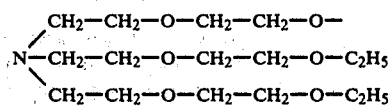

-continued

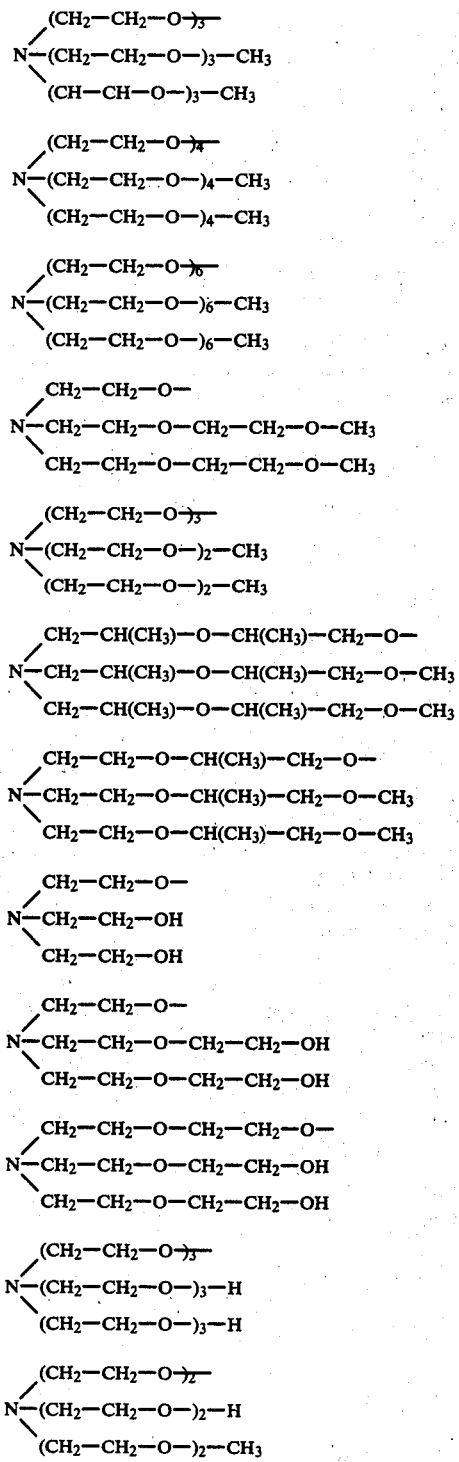

As indicated hereinabove, the active groups of the catalyst are fixed to a support, which is a cross-linked organic polymer. This support can be derived from any cross-linked organic polymer containing groups which can be substituted by the functional groups of the formula I.

Examples of polymers suitable for the preparation of the catalysts used in the present invention are polymers derived from vinylaromatic compounds, such as styrene and methylstyrene, and copolymers of vinylaromatic compounds and conjugated dienes having from 4 to 6 carbon atoms, such as copolymers of styrene and butadiene or isoprene.

Polystyrene is particularly suitable as the organic polymer, the cross-linking thereof advantageously being by means of divinylbenzene. The degree of cross-linking is an important factor. In fact, it is necessary for the active groups of the catalyst, represented by the formula I and grafted to the polymer, to be accessible. In other words, the degree of cross-linking must be sufficiently low not to prevent the molecules of reactants, and, if appropriate, of an auxiliary substance or a solvent, from penetrating into the polymer. For this reason, it is recommended that there be used a polystyrene having a degree of cross-linking of less than about 10% and advantageously of less than 5%.

The chlorine or bromine of the chloromethyl or bromomethyl radical (—CH$_2$Cl or —CH$_2$Br) borne by the benzene nucleus of the polystyrene is exemplary of suitable groups which can be thus substituted.

The percentage of benzene nuclei in the polystyrene which carry a functional group is preferably more than 5% and a percentage of more than 10% is particularly advantageous. The preferred supported catalysts can be represented by the following formula:

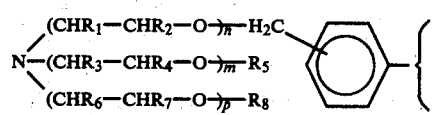

in which R$_1$ to R$_8$, n, m and p are as defined above and

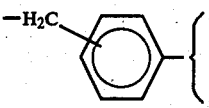

is derived from the chloromethylated or bromomethylated polystyrene having the formula:

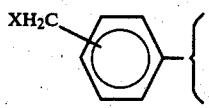

in which X represents a chlorine or bromine atom.

To prepare the catalysts used in the present process, a compound having the formula:

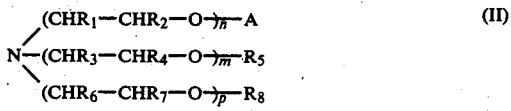

(II)

in which A represents an alkali metal and R$_1$ to R$_8$, n, m and p are as defined above, is reacted with a cross-linked organic polymer containing groups which can be substituted, as defined above, at a temperature on the order of 20° to 150° C., in an aprotic solvent.

A convenient method of preparation comprises the use of a compound of the formula (II) in which A represents sodium or potassium.

Another method which is more particularly suitable for the said preparation comprises the use of a solvent selected from among the group comprising benzene, toluene, N-methylpyrrolidone, hexamethylphosphorotriamide, dioxane, tetrahydrofuran, dimethoxyethane and sulfolane.

According to a preferred embodiment of the invention, a chloromethylated or bromomethylated polystyrene having a degree of cross-linking by divinylbenzene of less than 10%, and having a chlorine or bromine number of between about 0.5 and about 7 milliequivalents of chlorine or bromine per gram, is reacted with the compound of the formula (II).

Compounds of the aforesaid formula (II) can be obtained, for example, by reacting the alkali metal (for example, sodium metal), in an organic solvent medium, such as toluene, tetrahydrofuran, dioxane, or the like, at a temperature ranging from about 60° to 90° C., for 4 to 6 hours, with the aminoalcohol having the formula:

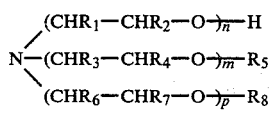
(III)

which is itself obtained by reacting a polyalkylene glycol having the formula:

$$HO-(CHR_1-CHR_2-O-)_n-H$$

in which $R_1$, $R_2$ and n are as defined above, with a bis-(polyoxaalkylamine) having the formula:

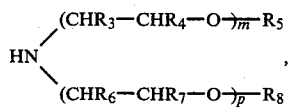

in which $R_3$ to $R_8$, m and p are as defined above, the molar ratio of the polyalkylene glycol to the bis-(polyoxaalkylamine) being equal to at least 1.5, in the presence of a hydrogenation/dehydrogenation catalyst, at a temperature ranging from 120° to 220° C. and preferably from 150° to 200° C. Nickel catalysts of the Raney or Harshaw nickel type can be used as the catalyst, the amount of catalyst generally ranging from 1 to 15% by weight and preferably from 2 to 6%. The molar ratio of the polyalkylene glycol to the bis-(polyoxaalkylamine) preferably ranges from 1.5 to 10 and even more advantageously ranges from 2 to 6. The presence of hydrogen under autogenous pressure, in an amount of 1 to 10% (by weight) of hydrogen, relative to the polyalkylene glycol used, also proves advantageous.

The supported catalysts comprising a cross-linked organic polymeric support and a plurality of functional groups (active groups) fixed to the said support and corresponding to the formula (I) per the above have proved particularly effective in the synthesis of glycidyl polyethers of polyphenols from alkali metal salts of polyphenols and 1-halogeno-2,3-epoxyalkanes.

The process according to the present invention requires the use of at least one alkali metal salt of a polyphenol. By the term "alkali metal salts of polyphenols" there are intended compounds having the structural formula:

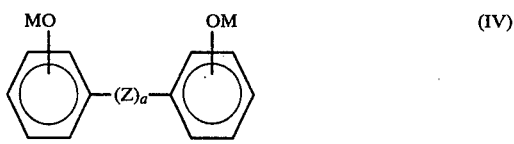
(IV)

in which a is equal to 0 or 1, M represents a lithium, sodium, potassium or cesium atom, M preferably being a sodium or potassium atom, and Z represents a divalent radical selected from the group comprising the radicals —SO$_2$—,

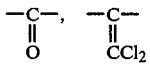

and the radicals of the formula (V) below:

$$\begin{array}{c} R_9 \\ | \\ -C- \\ | \\ R_{10} \end{array} \quad (V)$$

in which $R_9$ is a hydrogen atom or a methyl radical and $R_{10}$ represents hydrogen or a monovalent radical selected from the group comprising the radicals —CH$_3$, —CH$_2$—CH$_3$, —C(CH$_3$)$_3$, —CCl$_3$,

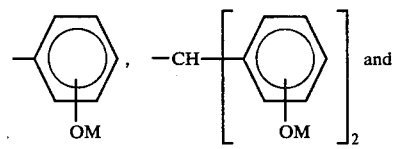

in which b is equal to 0, 1 or 2 and M is as defined above.

The following are exemplary of polyphenols which can be used in the form of their alkali metal salts, within the scope of the present invention: 4,4'-dihydroxybiphenyl, 4,4'-dihydroxydiphenylsulfone, 2,4'-dihydroxydiphenyldimethylmethane, 4,4'-dihydroxy-diphenylmethane (bisphenol F), 1,1-bis-(4-hydroxyphenyl)-ethane, 1,1-bis-(4-hydroxyphenyl)-isobutane, 2,2-bis-(4-hydroxyphenyl)-propane (bisphenol A), 2,2-bis-(4-hydroxyphenyl)-butane, 2,2-bis-(2-hydroxyphenyl)-propane, 2,2-bis-(4-hydroxyphenyl)-1,1,1-trichloroethane, 2,2-bis-(4-hydroxyphenyl)-1,1-dichloroethylene, tris-(4-hydroxyphenyl)-methane, 1,1,2,2-tetrakis-(4-hydroxyphenyl)-ethane, 2,2,3,3-tetrakis-(4-hydroxyphenyl)-ethane, 2,2,3,3-tetrakis-(4'-hydroxyphenyl)-butane, 2,2,4,4-tetrakis-(4'-hydroxyphenyl)-pentane and 2,2,5,5-tetrakis-(4'-hydroxyphenyl)-hexane.

The process according to the invention also envisages the use of alkali metal salts of polycyclic phenols in which some of the hydrogen atoms in the nucleus have been replaced by halogen atoms or alkyl radicals. This is the case, for example, of 2,2-bis-(3,5-dibromo-4- hydroxyphenyl)-propane, 2,2-bis-(3,5-dichloro-4-hydroxyphenyl)-propane, 2,2-bis(4-hydroxy-2-methylphenyl)-propane, 2,2-bis-(2-hydroxy-4-tert.-butylphenyl)-propane and 2,2-bis-(2-chloro-4-hydroxyphenyl)-propane.

The process according to the invention also envisages the use of alkali metal salts of more complex polycyclic phenols, such as the novolak resins. These resins are obtained by condensing phenol or cresol with aldehydes such as formaldehyde, acetaldehyde, crotonaldehyde or the like, in the presence of acid catalysts.

According to the present invention, it too is envisaged to use mixtures of two or more alkali metal salts of polyphenols, namely, a mixture of two or more compounds which differ in the nature of the alkali metal cation and/or are derived from two or more different polyphenols.

According to a preferred embodiment of the present invention, an alkali metal salt of a diphenol, or a mixture of two or more alkali metal salts of diphenols which can differ in the nature of the alkali metal cation and/or are derived from two or more different diphenols, is used. Sodium or potassium salts of one or more diphenols, in particular the salts of diphenols selected from the group comprising: bisphenol A, bisphenol F, 2,2-bis-(4-hydroxyphenyl)-1,1-dichloroethylene and 2,2-bis-(3,5-dibromo-4-hydroxyphenyl)-propane, are preferably used.

According to another preferred embodiment of the invention, the alkali metal salts of bisphenol A and/or bisphenol F, and more particularly the sodium or potassium salts, are used.

The sodium salts of bisphenol A and/or bisphenol F are particularly suitable for carrying out the present invention. The sodium salt of bisphenol A is very particularly preferred.

The amount of catalyst to be used is not critical.

Good results are observed when at least 0.05 equivalent of active groups of the formula (I) is used per 100 equivalents of OM groups originating from the alkali metal salts of polyphenols. No particular advantage is realized by using more than 5 equivalents per 100 equivalents of OM groups.

Preferably, from 0.25 to 2.5 equivalents of the formula (I) are used per 100 equivalents of OM groups.

According to yet another preferred embodiment of the present invention, when potassium salts of polyphenols are used, catalysts in which the functional groups are represented by the formula (I) in which $R_1$ to $R_4$, $R_6$ and $R_7$ represent a hydrogen atom, $R_5$ and $R_8$, which are identical, represent a hydrogen atom or, preferably, an alkyl radical having from 1 to 4 carbon atoms, and m, n and p are greater than or equal to 2, are used conjointly.

According to an even more preferred embodiment, sodium salts of polyphenols and catalysts in which the functional groups are represented by the formula (I) in which $R_1$ to $R_4$, $R_6$ and $R_7$ represent a hydrogen atom, $R_5$ and $R_8$, which are identical, represent a hydrogen atom or, preferably, an alkyl radical having from 1 to 4 carbon atoms, and m, n and p are greater than or equal to 1, are used.

Numerous 1-halogeno-2,3-epoxyalkanes are suitable for carrying out the present invention. Exemplary are 1-chloro-2,3-epoxypropane (more commonly referred to as epichlorohydrin), 1-bromo-2,3-epoxypropane, 1-chloro-2,3-epoxybutane, 1-chloro-2-methyl-2,3-epoxypropane, and also mixtures thereof.

According to another preferred embodiment of the invention, epichlorohydrin is utilized.

The term "essentially aprotic medium" is to be understood as connoting a medium which contains virtually no protons except for those which can originate from certain catalysts.

According to a first embodiment of the present invention, in an essentially aprotic medium, at least one mol of 1-halogeno-2,3-epoxyalkane is reacted per gram equivalent of OM groups originating from at least one starting material alkali metal salt of a polyphenol.

It has been determined that no particular advantage is gained by carrying out the reaction with more than 13 mols of 1-halogeno-2,3-epoxyalkane per gram equivalent of OM groups. The reaction is preferably carried out with 1 to 5 mols of 1-halogeno-2,3-epoxyalkane per gram equivalent of OM groups.

Since the alkali metal salts of polyphenols are insoluble in the 1-halogeno-2,3-epoxyalkanes, it is desirable to carry out the reaction with adequate stirring.

According to a second embodiment of the present invention, the alkali metal salt (or salts) can be introduced gradually, for example, in a variable number of equal or different portions, at intervals of varying length, or continuously.

The reaction temperature is not critical and typically ranges from 50° to 150° C. Below 50° C., the reaction is relatively slow, and above 150° C., there is a risk of degrading the resulting resin to a greater or lesser extent.

The reaction is preferably carried out at a temperature ranging from about 70° to 120° C.

The addition of at least one aprotic, and preferably polar, organic compound to the reaction medium is of great value, even when amounts on the order of but a few percent by weight are present in the reaction medium. The following are exemplary of organic compounds which can be used within the scope of the subject process: N-methylpyrrolidone, dimethylformamide, dimethylacetamide, dimethylsulfoxide, dipropylsulfoxide, tetramethylenesulfone, acetonitrile, propionitrile, benzonitrile and ethylene sulfide. Surprisingly certain of these compounds will render the reaction medium homogeneous, but in no case is homogeneity necessary.

When the reaction is carried out in the presence of an organic compound of this type, good results are obtained even when the amount of 1-halogeno-2,3-epoxyalkane is less than or equal to 3 mols per gram equivalent of OM groups, and this circumscribes an especially preferred embodiment of the present process.

In general, the amount of anhydrous, aprotic and polar organic compound added to the reaction medium is on the order of 10% by weight; this amount preferably represents at least 20% (by weight) of the reaction medium. Larger amounts thereof can be used, but it has been found that no particular advantage is gained beyond 80% (by weight).

According to another preferred embodiment of the invention, the reaction is carried out with 10 to 80% by weight of acetonitrile, and, preferably, with at least 30% by weight of acetonitrile.

The reaction can also be carried out under autogenous pressure, or under a nitrogen pressure which can be as much as 20 bars.

The use, according to the present invention, of a supported catalyst consisting of a cross-linked organic polymeric support and a plurality of functional groups affixed to this support and represented by the formula (I) provides the advantage that, upon completion of the reaction, the said catalyst can easily be separated from the reaction medium. In fact, this separation can be carried out simply by decantation and filtration. Moreover, it is possible to recycle this catalyst one or more times without observing a substantial drop in efficiency; upon completion of the reaction, the catalyst is recovered by any suitable means and the alkali metal halide by-product is removed, for example, by washing with water. It is not necessary to purify and/or dry this catalyst, which may contain traces of product or of unconverted reactants and, if appropriate, of solvent. Furthermore, it too has been found that the resins prepared by the present process are only weakly colored and that their characteristics do not change significantly with time. In other words, the quality of the resins is improved and these resins remain virtually unchanged during storage.

The process according to the invention is suitable, in particular, for the preparation of liquid epoxide resins from epichlorohydrin and alkali metal salts of bisphenol A and/or bisphenol F, and, more particularly, from the disodium salt of bisphenol A, in the presence of a supported catalyst consisting of a chloromethylated copolymer of styrene and divinylbenzene, in which the degree of cross-linking is less than 10% and in which the chlorine number is on the order of 0.5 to 7 meq/g, and of a plurality of functional groups tethered to the said support and having the formula:

$$N \begin{cases} CH_2-CH_2-O-CH_2-CH-O- \\ CH_2-CH_2-O-CH_2-CH_2-O-CH_3 \\ CH_2-CH_2-O-CH_2-CH_2-O-CH_3 \end{cases} \quad \text{or}$$

$$N \begin{cases} (CH_2-CH_2-O)_3- \\ (CH_2-CH_2-O)_2-CH_3 \\ (CH_2-CH_2-O)_2-CH_3 \end{cases}$$

This type of resin typically has a viscosity, measured at 25° C., which is less than or equal to 150 poises and an epoxide number on the order of 0.5 per 100 g.

In order to further illustrate the present invention and the advantages thereof, the following specific examples are given, it being understood that same are intended only as illustrative and in nowise limitative.

EXAMPLES

Preparation of the disodium salt of bisphenol A (referred to as "sodium bis-phenate" in the examples below):

883.5 g (3.87 mols) of bisphenol A were added to a solution of 310 g (7.74 mols) of sodium hydroxide in 2,407 cm³ of methanol. The mixture was heated under reflux for 30 minutes and about 70% of the methanol was then distilled. 3,000 cm³ of acetone were added to the remaining paste, and the suspension of the disodium salt of bisphenol A was filtered. After washing, the salt was dried in an oven under a pressure of 5 mm Hg for 24 hours at 50° C. (first batch) or at 25° C. (second batch).

Preparation of the catalysts:

(i) Preparation of tris-(3,6-dioxaoctyl)-amine (catalyst used in control experiment "b" below):

This catalyst was prepared from tris-(2-chloroethyl)-amine hydrochloride and sodium 2-ethoxyethanolate as follows:

450 g of 2-ethoxyethanol (5 mols) were introduced into a one liter three-necked round-bottomed flask fitted with a mechanical stirrer, a thermometer and a condenser. 23 g of sodium (1 mol) were added over the course of 3 hours, the temperature of the mixture being maintained at 40° C.

51.6 g of tris-(2-chloroethyl)-amine hydrochloride (namely, 0.215 mol) were added to the mixture thus obtained. The mixture was then heated at the reflux temperature of the 2-ethoxyethanol for 12 hours and the solvent was then distilled under reduced pressure. The excess sodium 2-ethoxyethanolate was neutralized by adding 12 cm³ of aqueous HCl (10 N).

The sodium chloride formed was filtered off and the solution was distilled. The tris-(3,6-dioxaoctyl)-amine distilled between 200° C. under a pressure of 1 mm Hg.

(ii) Preparation of 8-N-(8'-hydroxy-3'-6'-dioxaoctyl-aza-2,5-11,14-tetraoxapentadecane (the aminoalcohol used in the preparation of catalyst no. 2 below), having the formula:

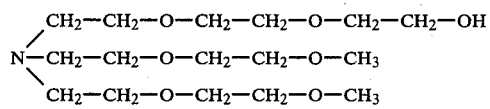

890 g (6 mols) of triethylene glycol, 160 g of dried Raney Ni and 442 g (2 mols) of 8-aza-2,5,11,14-tetraoxapentadecane were introduced into a 2 liter four-necked round-bottomed flask equipped with a stirrer, a hydrogen inlet, a column and a condenser for collecting the water.

The mixture was stirred under a stream of hydrogen (1 liter minute) and heated for 3 hours at 180° C. After filtering off the nickel and distilling the filtrate to remove the triethylene glycol, 508 g of the expected aminoalcohol, which had a boiling point of 193° C. under a pressure of 0.3 mm Hg, were recovered.

NB: 8-N-(5'-hydroxy-3'-oxapentyl)-aza-2,5,11,14-tetraoxapentadecane, which is the aminoalcohol used in the preparation of catalyst no. 1 below, was prepared in a similar manner.

(iii) Preparation of catalyst no. 1 (the catalyst used in Example 1 below):

300 cm³ of anhydrous toluene, 36.05 g of 8-N-(5'-hydroxy-3'-oxapentyl)-aza-2,5,11,14-tetraoxapentadecane and 2.41 g of sodium were successively introduced into a 250 ml three-necked reactor equipped with a magnetic stirrer, a reflux condenser and a nitrogen inlet. After heating at 60° C. for 20 hours and at 90° C. for 4 hours, the sodium had totally reacted. The mixture was then cooled to 60° C. and 52 g of polystyrene, cross-linked by 2% of divinylbenzene and containing 1.3 meq of chlorine/g, were then introduced.

After 40 hours at 60° C. under a nitrogen atmosphere, the polymer was cooled. It was then filtered off and washed with water (to remove the occluded salts therefrom) and with methanol. The resulting product was subsequently dried in vacuo at 50° C.

The above procedure yielded 66 g of an aminoether grafted onto polystyrene, the general formula of which can be represented as follows:

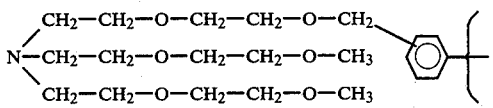

The degree of grafting was 75%. According to the nitrogen number, this compound contained 0.929 milliequivalent (meq) of functional groups per gram.

(iv) Preparation of catalyst no. 2 (the catalyst used in Example 2 below):

100 cm³ of anhydrous toluene, 9.1 g of 8-N-(8'-hydroxy-3',6'-dioxaoctyl)-aza-2,5,11,14-tetraoxapentadecane and 0.5 g of sodium metal were successively introduced into a 250 ml three-necked reactor equipped with a magnetic stirrer, a reflux condenser and a nitrogen inlet. After stirring for 7 hours at 60° C., the sodium had totally disappeared. 5 g of polystyrene, cross-linked by 2% of divinylbenzene and containing $4.10^{-3}$ chloromethyl groups per gram of polymer (4 meq of chlorine/g), were then introduced.

The mixture was heated at 60° C. for 48 hours under a nitrogen atmosphere. After cooling, the polymer was filtered off and washed with water (to remove the occluded salts) and then with methanol.

The product was subsequently dried in vacuo at 50° C.

This yielded 8.8 g of an aminoether grafted onto polystyrene, the general formula of which can be represented as follows:

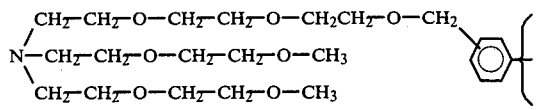

The degree of grafting was 64%.

In the control experiments and in Example 1 below, sodium bis-phenate originating from the first batch was used.

Control experiment (a):

This experiment illustrates the preparation of an epoxide resin from sodium bis-phenate and epichlorohydrin in the absence of a catalyst.

92.5 g (1 mol) of epichlorohydrin and 56.4 cm³ of acetonitrile were introduced into a glass reactor equipped with a central anchor stirrer, a bulb condenser and a thermometer. The mixture was heated to 60° C. and 54.4 g (0.2 mol) of anhydrous sodium bis-phenate were added. This provided a suspension, which was heated at 83° C. (reflux temperature of the acetonitrile) for 1 hour. The suspension was filtered and the filtrate was evaporated under reduced pressure (20 mm Hg) by heating to 140° C.

27.2 g of a resin having the following characteristics:
Viscosity measured at 25° C.=240 poises
Epoxide number per 100 g=0.512
Coloration=7 on the Garner scale were recovered.

This resin did not change during storage; after 100 days, the viscosity (at 25° C.) was 255 poises.

Control experiment (b):

This experiment illustrates the preparation of an epoxide resin from sodium bis-phenate and epichlorohydrin in the presence of a non-supported catalyst.

92.5 g (1 mol) of epichlorohydrin, 57.7 cm³ of acetonitrile and 3.65 g (10 mmols) of tris-(3,6-dioxaoctyl)-amine were introduced into the apparatus described above. The mixture was heated to 60° C. and 54.4 g (0.2 mol) of anhydrous sodium bis-phenate were added. This provided a suspension, which was heated at 83° C. (reflux temperature of the acetonitrile) for 1 hour. The suspension was filtered and the filtrate was evaporated under reduced pressure (20 mm Hg) by heating to 140° C.

65.4 g of a resin having the following characteristics:
Viscosity measured at 25° C.=85 poises
Epoxide number per 100 g=0.506
Coloration=13 on the Garner scale
Basicity (measured by determination with perchloric acid)=0.1550 meq/g were recovered.

This resin changed during storage; after 10 days; the viscosity (at 25° C.) was 2,480 poises.

EXAMPLE 1

Control experiment "b" above was repeated, except that 10.76 g of catalyst no. 1 described above were used, namely, 10 meq of functional groups; the volume of acetonitrile was 61 cm³.

This provided 48.8 g of a liquid resin having the following characteristics:
Viscosity measured at 25° C.=120 poises
Epoxide number per 100 g=0.537
Coloration=5 on the Garner scale
Basicity (measured by determination with perchloric acid)=0.0065 meq/g This resin was stable during storage; after 10 days, the viscosity (at 25° C.) was 120 poises.

Upon completion of the reaction, the catalyst (which was insoluble in the reaction medium) was recovered. Same was washed with methanol in order to dissolve the sodium bis-phenate which it may contain, and with water in order to dissolve the contaminating sodium chloride. The catalyst was then dried at 50° C. in vacuo; it could then be used in a further operation.

The sodium bis-phenate used in the examples below originates from the aforesaid second batch.

EXAMPLE 2

Using the equipment and the procedure described above, a resin was prepared from 92.5 g (1 mol) of epichlorohydrin, 66 cm³ of acetonitrile, 68.5 g of catalyst no. 2 described above, namely, 8.85 meq of functional groups, and 73.9 g (0.2 mol) of sodium bis-phenate (essentially anhydrous).

40.6 g of a resin having the following characteristics:
Viscosity measured at 25° C.=96 poises
Epoxide number per 100 g=0.539
coloration=11 on the Garner scale were recovered.

The viscosity (at 25° C.) was 93 poises after storage for 10 days.

EXAMPLE 3

Using the equipment and the procedure described above, a resin was prepared from 69.4 g (0.75 mol) of epichlorohydrin, 50 cm³ of acetonitrile, 6.58 g of catalyst recovered in Example 2, namely, 6.64 meq of functional groups, and 55.2 g (0.15 mol) of sodium bis-phenate (essentially anhydrous).

This provided 30 g of a resin having the following characteristics:
Viscosity measured at 25° C.=91 poises
Epoxide number per 100 g=0.548
Coloration=6 on the Garner scale The viscosity (at 25° C.) was 96 poises after storage for 10 days.

EXAMPLE 4

Example 3 above was repeated using 9.08 g of catalyst (namely, 6.64 meq of functional groups) recovered in Example 3.

This provided 29 g of a resin having the following characteristics:

Viscosity measured at 25° C.=90 poises
Epoxide number per 100 g=0.543
Coloration=7 on the Garner scale The viscosity (at 25° C.) was 98 poises after storage for 10 days.

EXAMPLE 5

Using the equipment and the procedure described above, a resin was prepared from 46.3 g (0.5 mol) of epichlorohydrin, 31 cm³ of acetonitrile, 8.57 g of catalyst recovered in Example 4, namely, 4.42 meq of functional groups, and 36.9 g (0.1 mol) of sodium bis-phenate (essentially anhydrous).

This provided 19 g of a resin having the following characteristics:

Viscosity measured at 25° C.=91 poises
Epoxide number per 100 g=0.538
Coloration=6 on the Garner scale The viscosity (at 25° C.) was 92 poises after storage for 10 days.

EXAMPLE 6

Example 5 above was repeated using 5.38 g of catalyst no. 1, the preparation of which was described above, namely, 5 meq of functional groups.

This provided 25.7 g of a resin having the following characteristics:

Viscosity measured at 25° C.=110 poises
Epoxide number per 100 g=0.557
Coloration=5 on the Garner scale The viscosity (at 25° C.) was 110 poises after storage for 10 days.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of glycidyl polyethers of polyphenols, comprising reacting at least one alkali metal salt of a polyphenol with at least one 1-halogeno-2,3-epoxyalkane, in an anhydrous and essentially aprotic reaction medium, and in the presence of a catalytically effective amount of a catalyst which comprises a cross-linked organic polymeric support, said support having a plurality of catalytically active functional groups covalently coupled thereto, the free valence of said functional groups having the structural formula:

$$N \begin{cases} (CHR_1-CHR_2-O)_{\overline{n}} \\ (CHR_3-CHR_4-O)_{\overline{m}}R_5 \\ (CHR_6-CHR_7-O)_{\overline{p}}R_8 \end{cases} \quad (I)$$

in which $R_1$, $R_2$, $R_3$, $R_4$, $R_6$ and $R_7$, which are identical or different, are each a hydrogen atom or an alkyl radical having from 1 to 4 carbon atoms, $R_5$ and $R_8$, which are identical or different, represent a hydrogen atom, an alkyl or cycloalkyl radical having from 1 to 12 carbon atoms, a phenyl radical or radical $C_6H_5-C_2H_{2q}-$ or $C_qH_{2q+1}-C_6H_4-$, in which q ranges from 1 to about 12, and n, m and p, which are identical or different, range from 1 to 10.

2. The process as defined by claim 1, wherein the formula (I), $R_1$, $R_2$, $R_3$, $R_4$, $R_6$ and $R_7$, which are identical or different, represent a hydrogen atom or a methyl radical and $R_5$ and $R_8$, which are identical or different, represent a hydrogen atom or an alkyl radical having from 1 to 4 carbon atoms.

3. The process are defined by claim 2, wherein the formula (I), n, m and p, which are identical or different, range from 1 to 6.

4. The process as defined by claim 1, the degree of cross-linking comprising said support being less than about 10%.

5. The process as defined by claim 4, said degree of cross-linking being less than about 5%.

6. The process as defined by claim 4, said support comprising a polystyrene polymer cross-linked with divinylbenzene.

7. The process as defined by claim 6, said support comprising chloromethylated or bromomethylated polystyrene.

8. The process as defined by claim 7, wherein the percentage of benzene nuclei comprising said polystyrene bearing a chloromethyl or bromomethyl substituent is greater than about 5%.

9. The process as defined by claim 8, said percentage being greater than about 10%.

10. The process as defined by claim 8, wherein the polystyrene has a bromine or chlorine number ranging from about 0.5 to about 7 milliequivalents of bromine or chlorine per gram.

11. The process as defined by claim 7, wherein said catalyst has the structural formula:

$$N \begin{cases} (CHR_1-CHR_2-O)_{\overline{n}}-H_2C \\ (CHR_3-CHR_4-O)_{\overline{m}}-R_5 \\ (CHR_6-CHR_7-O)_{\overline{p}}-R_8 \end{cases} - \bigcirc -$$

and further wherein $$-H_2C-\bigcirc-$$

is derived from a chloromethylated or bromomethylated polystyrene having the structural formula:

$$XH_2C-\bigcirc-$$

in which X represents a chlorine or bromine atom.

12. The process as defined by claim 7, wherein said catalyst has the structural formula:

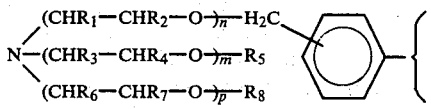

in which $R_1$ to $R_4$, $R_6$ and $R_7$ represent hydrogen, $R_5$ and $R_8$, which are identical, represent hydrogen or an alkyl radical having from 1 to 4 carbon atoms, m, n and p range from 1 to 6 and

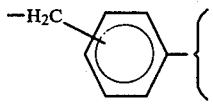

is derived from a chloromethylated or bromomethylated polystyrene cross-linked with divinylbenzene, said degree of cross-linking being less than about 10% and the chlorine or bromine number thereof ranging from about 0.8 to about 7 meq/g.

13. The process as defined by claim 1 or 12, wherein the reactant alkali metal salt of a polyphenol is a bis-alkali metal salt of bisphenol A, bisphenol F, 2,2-bis-(4-hydroxyphenyl)-1,1-dichloroethylene or 2,2-bis-(3,5-dibromo-4-hydroxyphenyl)-propane.

14. The process as defined by claim 13, wherein the reactant alkali metal salt of a polyphenol is a bis-alkali metal salt of bisphenol A, bisphenol F, or mixtures thereof.

15. The process as defined by claim 14, wherein the reactant alkali metal salt of a polyphenol is a bis-alkali metal salt of bisphenol A.

16. The process as defined by claim 13, wherein the reactant 1-halogeno-2,3-epoxyalkane is epichlorohydrin.

17. The process as defined by claim 1, wherein the reaction is carried out in the presence of 1 to 13 mols of the 1-halogeno-2,3-epoxyalkane per gram equivalent of OM groups comprising said alkali metal salt of the polyphenol.

18. The process as defined by claim 17, said reaction being carried out in the presence of 1 to 5 mols of the epoxyalkane.

19. The process as defined by claim 17, wherein said reaction is carried out in the presence of 0.05 to 5 equivalents of functional groups of the formula (I) per 100 equivalents of OM groups comprising said alkali metal salt of the polyphenol.

20. The process as defined by claim 19, said reaction being carried out in the presence of 0.25 to 2.5 equivalents of the functional groups having the formula (I).

21. The process as defined by claim 19, wherein said reaction is carried out in the presence of a polar aprotic organic compound selected from the group consisting of acetonitrile, dimethylformamide, dimethylacetamide, dimethyl sulfoxide, dipropyl sulfoxide, propionitrile, benzonitrile, ethylene sulfide, N-methylpyrrolidone and tetramethylenesulfone.

22. The process as defined by claim 21, said reaction being carried out in the presence of acetonitrile.

23. The process as defined by claim 17, the reaction being carried out at a temperature ranging from from 50° to 150° C.

24. The process as defined by claim 23, said reaction being carried out at a temperature ranging from 70° to 120° C.

* * * * *